(12) United States Patent
Sondbø et al.

(10) Patent No.: US 7,678,930 B2
(45) Date of Patent: Mar. 16, 2010

(54) PROCESS FOR DECREASING THE AMOUNT OF CHOLESTEROL IN A MARINE OIL USING A VOLATILE WORKING FLUID

(75) Inventors: Sverre Sondbø, Sandefjord (NO); Olav Thorstad, Porsgrunn (NO)

(73) Assignee: Pronova Biopharma Norge AS, Baerum (NO)

( * ) Notice: Subject to any disclaimer, the term of this patent is extended or adjusted under 35 U.S.C. 154(b) by 912 days.

(21) Appl. No.: 10/520,897

(22) PCT Filed: Jul. 11, 2003

(86) PCT No.: PCT/IB03/02776

§ 371 (c)(1),
(2), (4) Date: Jul. 25, 2005

(87) PCT Pub. No.: WO2004/007655

PCT Pub. Date: Jan. 22, 2004

(65) Prior Publication Data

US 2006/0134303 A1    Jun. 22, 2006

(30) Foreign Application Priority Data

Jul. 11, 2002   (SE) .................................... 0202188
Jul. 8, 2003   (WO) ...................... PCT/IB/03/02827

(51) Int. Cl.
*C11B 1/00*    (2006.01)
(52) U.S. Cl. ...................................................... 554/12
(58) Field of Classification Search .................... 554/12
See application file for complete search history.

(56) References Cited

U.S. PATENT DOCUMENTS 2,126,467 A    8/1938   Hickman et al.
2,146,894 A    2/1939   Hickman (Continued)

FOREIGN PATENT DOCUMENTS

AT          328597          3/1976

(Continued)

OTHER PUBLICATIONS

Bimbo, A.P., "Guidelines for Characterizing Food-grade Fish Oil," Inform, vol. 9, No. 5, 473-483 (May 1998).

(Continued)

*Primary Examiner*—Deborah D Carr
(74) *Attorney, Agent, or Firm*—Finnegan, Henderson, Farabow, Garrett & Dunner, L.L.P.

(57) ABSTRACT

The invention relates to a process for decreasing the amount of cholesterol in a mixture comprising a marine oil, the marine oil containing the cholesterol, which process comprises the steps of adding a volatile working fluid to the mixture, where the volatile working fluid comprises at least one of a fatty acid ester, a fatty acid amide and a hydrocarbon, and subjecting the mixture with the added volatile working fluid to at least one stripping processing step, in which an amount of cholesterol present in the marine oil in free form is separated from the mixture together with the volatile working fluid. The present invention also relates to a volatile cholesterol decreasing working fluid and a health supplement and a pharmaceutical, based on a marine oil, prepared according to the process mentioned above.

23 Claims, 1 Drawing Sheet

U.S. PATENT DOCUMENTS

| | | | |
|---|---|---|---|
| 2,180,356 A | 11/1939 | Hickman | |
| 2,349,269 A | 5/1944 | Hickman | |
| 2,985,589 A | 5/1961 | Broughton et al. | |
| 3,082,228 A | 3/1963 | Sutherland | |
| 3,158,541 A | 11/1964 | Sutherland | |
| 3,696,107 A | 10/1972 | Neuzil | |
| 3,706,812 A | 12/1972 | de Rosset et al. | |
| 3,761,533 A | 9/1973 | Otani et al. | |
| 4,061,556 A | 12/1977 | Reis et al. | |
| 4,124,528 A | 11/1978 | Modell | |
| 4,147,624 A | 4/1979 | Modell | |
| 4,156,688 A | 5/1979 | Zosel | |
| 4,352,746 A | 10/1982 | Bracco et al. | |
| 4,377,525 A | 3/1983 | D'Alelio et al. | |
| 4,377,526 A | 3/1983 | Fujita et al. | |
| 4,415,554 A | 11/1983 | Horrobin | |
| 4,526,902 A | 7/1985 | Rubin | |
| 4,554,107 A | 11/1985 | Takao | |
| 4,564,475 A | 1/1986 | Masaichiro | |
| 4,615,839 A | 10/1986 | Seto et al. | |
| 4,623,488 A | 11/1986 | Takao | |
| 4,675,132 A | 6/1987 | Stout et al. | |
| 4,681,896 A | 7/1987 | Horrobin | |
| 4,692,280 A | 9/1987 | Spinelli et al. | |
| 4,758,592 A | 7/1988 | Horrobin et al. | |
| 4,764,392 A | 8/1988 | Yasufuku et al. | |
| 4,792,418 A | 12/1988 | Rubin et al. | |
| 4,804,555 A * | 2/1989 | Marschner et al. | 426/601 |
| 4,956,286 A | 9/1990 | Macrae | |
| 4,956,287 A | 9/1990 | Suzuki et al. | |
| 4,996,072 A * | 2/1991 | Marschner et al. | 426/417 |
| 5,013,443 A | 5/1991 | Higashidate et al. | |
| 5,091,117 A * | 2/1992 | Athnasios et al. | 554/193 |
| 5,106,542 A | 4/1992 | Traitler et al. | |
| 5,130,061 A | 7/1992 | Cornieri et al. | |
| 5,130,449 A | 7/1992 | Lagarde et al. | |
| 5,211,812 A | 5/1993 | Vielberth et al. | |
| 5,243,046 A | 9/1993 | Traitler et al. | |
| 5,316,927 A | 5/1994 | Zaks et al. | |
| 5,340,602 A | 8/1994 | Hoche | |
| 5,374,751 A | 12/1994 | Cheng et al. | |
| 5,436,018 A * | 7/1995 | Massie et al. | 426/417 |
| 5,480,787 A | 1/1996 | Negishi et al. | |
| 5,502,077 A | 3/1996 | Breivik et al. | |
| 5,558,893 A | 9/1996 | Muraldihara | |
| 5,656,667 A | 8/1997 | Breivik et al. | |
| 5,698,594 A | 12/1997 | Breivik et al. | |
| 5,719,302 A | 2/1998 | Perrut et al. | |
| 5,792,795 A | 8/1998 | Buser et al. | |
| 5,945,318 A | 8/1999 | Breivik et al. | 435/134 |
| 5,948,818 A | 9/1999 | Buser et al. | |
| 6,204,401 B1 | 3/2001 | Perrut et al. | |
| 6,277,405 B1 | 8/2001 | Stamm et al. | |
| 6,518,049 B1 | 2/2003 | Haraldsson et al. | |
| 2002/0077361 A1 | 6/2002 | Peet et al. | |
| 2003/0077342 A1 | 4/2003 | Maffetone | |
| 2003/0212138 A1 | 11/2003 | Obukowicz | |
| 2004/0210070 A1 | 10/2004 | Kruidenberg | |
| 2005/0171200 A1 | 8/2005 | Calder et al. | |
| 2005/0256326 A1 | 11/2005 | Breivik et al. | |
| 2006/0148047 A1 | 7/2006 | Haraldsson et al. | |
| 2006/0166935 A1 | 7/2006 | Bryhn | |
| 2006/0211762 A1 | 9/2006 | Rongen et al. | |
| 2007/0036862 A1 | 2/2007 | Rongen et al. | |
| 2008/0234375 A1 | 9/2008 | Breivik et al. | |
| 2009/0118524 A1 | 5/2009 | Albers et al. | |

FOREIGN PATENT DOCUMENTS

| | | |
|---|---|---|
| AT | 347551 | 1/1979 |
| CA | 2260397 | 7/2000 |
| CL | 42559 | 10/1998 |
| CN | 1143384 A | 2/1997 |
| DE | 2 332 038 C3 | 1/1974 |
| DE | 3 839 017 A1 | 5/1990 |
| DE | 40 08 066 A1 | 8/1991 |
| DE | 100 24 420 A1 | 11/2001 |
| DE | 10 2006 012 866 A1 | 4/2007 |
| EP | 0 175 468 A2 | 3/1986 |
| EP | 0 189 610 A1 | 8/1986 |
| EP | 0 283 140 B1 | 9/1988 |
| EP | 0 292 846 B1 | 11/1988 |
| EP | 0 255 824 B1 | 1/1990 |
| EP | 0 442 184 A1 | 8/1991 |
| EP | 0632267 A1 | 1/1995 |
| EP | 1 419 780 A1 | 5/2004 |
| FR | 2 103 302 | 4/1972 |
| FR | 2 527 934 | 12/1983 |
| FR | 2 651 148 A1 | 3/1991 |
| FR | 2 651 149 A1 | 3/1991 |
| FR | 2 686 028 A1 | 7/1993 |
| FR | 2 690 630 A1 | 11/1993 |
| FR | 2 694 208 A1 | 2/1994 |
| GB | 476134 | 12/1937 |
| GB | 485614 | 5/1938 |
| GB | 490433 | 8/1938 |
| GB | 493948 | 10/1938 |
| GB | 2 033 745 A | 5/1980 |
| GB | 1 604 554 | 12/1981 |
| GB | 2 148 713 A | 6/1985 |
| GB | 2 197 199 A | 5/1988 |
| GB | 2 218 984 A | 11/1989 |
| GB | 2 221 843 A | 2/1990 |
| JP | 59-14793 | 1/1984 |
| JP | 60-33088 | 2/1985 |
| JP | 61-192797 | 8/1986 |
| JP | 1-252294 | 10/1989 |
| JP | 2-25447 | 1/1990 |
| JP | 6-116585 | 4/1994 |
| JP | 6-293895 | 10/1994 |
| JP | 9-510091 | 10/1997 |
| JP | 39-05538 | 7/2003 |
| WO | WO 86/03781 | 7/1986 |
| WO | WO 87/02247 A1 | 4/1987 |
| WO | WO 87/03899 A1 | 7/1987 |
| WO | WO 88/08444 A1 | 11/1988 |
| WO | WO 89/11521 A1 | 11/1989 |
| WO | WO 90/12509 | 11/1990 |
| WO | WO 90/13656 | 11/1990 |
| WO | WO 91/16443 | 10/1991 |
| WO | WO 95/24459 | 9/1995 |
| WO | WO 98/18952 A1 | 5/1998 |
| WO | WO 00/73254 A1 | 12/2000 |
| WO | WO 01/03810 A2 | 1/2001 |
| WO | WO 2007/107260 A1 | 9/2007 |

OTHER PUBLICATIONS

Cmolik, J. et al., "Physical Refining of Edible Oils," *Eur. J. Lipid Sci. Technol.*, 102, 472-486 (2000).

Abbate, R. et al. "n-3 PUFA supplementation, monocyte PCA expression and interleukin-6 production," *Prostaglandins, Leukotrienes and Essential Fatty Acids* (1996), 54(6), 439-444.

Abe, Y. et al. "Soluble Cell Adhesion Molecules in Hypertriglyceridemia and Potential Significance on Monocyte Adhesion," *Arteriosclerosis, Thrombosis, and Vascular Biology* (1998), 18(5), 723-731.

Abhyankar, B. "Further reduction in mortality following myocardial infarction," *J. Hospital Medicine* (2002), 63(10), 610-614.

Ackman, R.G. "Oils and Fats Group International Lecture: The year of the fish oils," *Chemistry and Industry* (1988) 139-145.

Adachi, S. et al. "Acidolysis of Sardine Oil by Lipase to Concentrate Eicosapentaenoic and Docosahexaenoic Acids in Glycerides," *J. Ferment. Bioeng.* (1993), 75(4), 259-264.

Bimbo, A. P. "Processing of Fish Oils" in *Fish Oils in Nutrition*, M.E. Stansby, Ed. (1990) 181-225.
Blonk, "Dose-response effects of fish-oil supplementation in healthy volunteers," *Am. J. Clin. Nutr.* (1990), 52, 120-127.
Bønaa, K. H. et al. "Effect of Eicosapentaenoic and Docosahexaenoic Acids on Blood Pressure in Hypertension," *New England J. of Medicine* (1990), 322, 795-801.
Bousquet, O. et al. "Counter-current chromatographic separation of polyunsaturated fatty acids," *J. Chromatography A* (1995), 704, 211-216.
Braunwald et al. "Harrison's Principles of Medicine," 11th ed. (McGraw-Hill, New York, 1985) p. 1204.
Breivik, H. et al. "Preparation of Highly Purified Concentrates of Eicosapentaenoic Acid and Docosahexaenoic Acid," *J. Am. Oil. Chem. Soc.* (1997), 74(11), 1425-1429.
Breivik, H. "Production and Quality Control of n-3 Fatty Acids," *Clinical Pharmacology* (1992), 5, 25-39.
Bryhn, M. et al. "The bioavailability and pharmacodynamics of different concentrations of omega-3 acid ethyl esters," *Prostaglandins, leukotrienes and Essential Fatty Acids* (2006), 75, 19-24.
CAPLUS English Abstract for De Bernardi et al. *Acta Toxicol. Ther.* (1987), 8(3), 339-352; Accession No. 1988:604885.
Calabresi, L. et al. "Omacor in familial combined hyperlipidemia : Effects on lipids and low density lipoprotein subclasses," *Atherosclerosis* (2000), 148(2), 387-396.
Chan, D. C. et al "Regulatory Effects of HMG CoA Reductase Inhibitor and Fish Oils on Apolipoprotein B-100 Kinetics in Insulin-Resistant Obese Male Subjects With Dyslipidemia," *Diabetes* (2002), 51, 2377-2386.
Cvengros, J. "Physical Refining of Edible Oils," *J. Am. Oil Chem. Soc.* (1995), 72(10), 1193-1196.
Database WPI: Week 199022, Derwent Publications Ltd., DE 3839017, 1990.
Database WPI: Week 198001, Derwent Publications Ltd., DE 2332038, 1980.
Database WPI: Week 197402, Derwent Publications Ltd., DE 2332038, 1974.
Database WPI: Week 199346, Derwent Publications Ltd., FR 2694208, 1993.
Database WPI: Week 199329, Derwent Publications Ltd., FR 2686028, 1993.
Database WPI: Week 199110, Derwent Publications Ltd., FR 2651148, 1991.
Database WPI: Week 199110, Derwent Publications Ltd., FR 2651149, 1991.
Database WPI: Week 198403, Derwent Publications Ltd., FR 2527934, 1984.
Database WPI: Week 197228, Derwent Publications Ltd., FR 2103302, 1972.
Database WPI: Week 198514, Derwent Publications Ltd., JP 60033088, 1985.
Database WPI: Week 198641, Derwent Publications Ltd., JP 61192797, 1986.
Database WPI: Week 198410, Derwent Publications Ltd., JP 59014793, 1984.
Database WPI: Week 198946, Derwent Publications Ltd., JP 1252294, 1989.
Database WPI: Week 200417, Derwent Publications Ltd., JP 3905538, 2004.
Database WPI: Week 199542, Derwent Publications Ltd., JP 9510091, 1995.
Database WPI: Week 199502, Derwent Publications Ltd., JP 6-293895, 1995.
Database WPI: Week 199421, Derwent Publications Ltd., JP 6116585, 1994.
Database WPI: Week 199010, Derwent Publications Ltd., JP 2025447, 1990.
De Bernardi et al. "Study of Perinatal and Postnatal Effects in Rats After Oral Administration with a New Drug Containing Eicosapentaenoic Acid and Docosahexaenoic Acid at 85%," *Acta Toxicol. Ther.* (1987), 8(3), 339-352, Abstract.
Derwent abstract of ZA 198905758.
Diep, Q. N. et al "Docosahexaenoic Acid, a Peroxisome Proliferator-Activated Receptor-a Ligand, Induces Apoptosis in Vascular Smooth Muscle Cells by Stimulation of p38 Mitogen-Activated Protein Kinase," *Hypertension* (2000), 36, 851-855.
Donadio, J. V. "Use of fish oil to treat patients with immunoglobulin A nephropathy" *Am. J. Clin. Nutr.* (2000), 71(Suppl), 373S-375S.
Donadio, J. V. et al. "A Randomized Trial of High-Dose Compared with Low-Dose Omega-3 Fatty Acids in Severe IgA Nephropathy," *J. Am. Soc. Nephrol.* (2001), 12(4), 791-799.
Durrington, P. N. et al. "An omega-3 polyunsaturated fatty acid concentrate administered for one year decreased triglycerides in simvastatin treated patients with coronary heart disease and persisting hypertriglyceridaemia," *Heart* (2001), 85(5), 544-548.
English translation of AT 328597, 1976.
English translation of CL 42559, 1998.
EPAX marketing information (7 pages), 2000.
EPAX production information (6 pages), 2000.
Franzosi, M. G. et al "Cost-Effectiveness Analysis of n-3 Polyunsaturated Fatty Acids (PUFA) after Myocardial Infarction," *Pharmacoeconomics* (2001), 19(4), 411-420.
Gauglitz, E.J. et al. "Adsorptive Bleaching and Molecular Distillation of Menhaden Oil," *Journal of the American Oil Chemists Society* (1965), 42, 561-563.
Gissi-Prevenzione Investigators "Dietary supplementation with n-3 polyunsaturated fatty acids and vitamin E after myocardial infarction: results of the GISSI-Prevenzione trial," *Lancet* (1999), 354, 447-455.
Hamazaki, T. et al. "Effects of fish oil rich in eicosapentaenoic acid on serum lipid in hyperlipidemic hemodialysis patients," *Kidney International* (1984), 26(1), 81-84.
Haraldsson, G. G. et al. "Studies on the Positional Specificity of Lipase from *Mucor miehei* During Interesterifcation Reactions of Cod Liver Oil with n-3 Polyunsaturated Fatty Acid and Ethyl Ester Concentrations," *Acta Chemica Scandinavica* (1991), 45, 723-730.
Haraldsson, G. G. et al. "Separation of Eicosapentaenoic Acid and Docosahexaenoic Acid in Fish Oil by Kinetic Resolution Using Lipase," *J. Am. Oil Chem. Soc.* (1998), 75(11), 1551-1556.
Haraldsson, G. G. et al. "The Preparation of Concentrates of Eicosapentaenoic Acid an Docosahexaenoic Acids by Lipase-Catalyzed Transesterification of Fish Oil with Ethanol," *J. Am. Oil. Chem. Soc.* (1997), 74(11), 1419-1424.
Harris , W. S. et al. "Safety and efficacy of Omacor in sever hypertriglyceridemia," *Journal of Cardiovascular Risk* (1997), 4(5-6), 385-391.
Hellström, "Some Foreign Recommendations on the Treatment of Hyper-lipidaemias," in *Treatment of Hyperlipidemia*, National Board of Health and Welfare Drug Information Center, Sweden (1989) 131-137.
Hellström "Treatment of Hyperlipidemia: Opinions and recommendations from the group," in *Treatment of Hyperlipidemia*, National Board of Health and Welfare Drug Information Committee, Sweden (1989) 147-158.
Hogg, R. J. et al. "Advances in Treatment: Immunoglobulin A Nephropathy," *Seminars in Nephrology* (1996), 16(6) 511-516.
Hoshino, T. et al. "Selective Hydrolysis of Fish Oil by Lipase to concentrate N-3 Polyunsaturated Fatty Acids," *Agric. Biol. Chem.* (1990), 54(6), 1459-1467.
Information from http://www.epax.com (6 pages), 2000.
Information from http://www.omacor.com (25 pages), 2000.
Information from http://www.omacorrx.com (45 pages), 2000.
Japanese Litigation, Demand for Trial dated Aug. 31, 2007.
Johansen, O. et al. "n-3 Fatty Acids Do Not Prevent Restenosis After Coronary Angioplasty: Results from the CART Study," *Journal of the American College of Cardiology* (1999), 33(6), 1619-1626.
Julshamn, K. et al. "Removal of DDT and its metabolites from fish oils by molecular distillation," *Fiskeridirektoratets Skrifter Serie Teknologiske Undersøkelser* (1978), 5(15), 3-11.
Kanematsu et al "Studies on the behaviour of trace components in oils and fats during processing for edible use. I. Removal of organochlorine pesticides and polychlorinated biphenyls (PCB) from oils and fats," *J. of Japan. Oil Chemists' Society* (1976), 25(1), 38-41, Abstract.

Kinsella et al. *Seafoods and Fish Oils in Human Health and Disease* (New York, Marcel Dekka Inc. 1987) pp. 7-9.

Kris-Etherton et al. "Fish Consumption, Fish Oil, Omega-3 Fatty Acids, and Cardiovascular Disease," *Circulation* (2002), 106, 2747-2757.

Kuk, M. S. "Supercritical carbon dioxide extraction of cottonseed with co-solvents," *J. Am. Oil Chem. Soc.* (1994), 71(12), 1353-1356.

Larsen et al. "Biosynthesis of Alginate," *Int. Seaweed Symp.* 7th (1971), 491-495.

Lie, E. et al. "Esterification of polyunsaturated fatty acids with lipases from different sources," *International J. of Food Science and Technology* (1992), 27, 73-76.

Lie, et al. "Fatty Acid Specificity of Candida cylindracea Lipase," *Feet, Seifen, Anstrichmittel* (1986), 88(9), 365-367.

Lim, G. P. et al. "A Diet Enriched with the Omega-3 Fatty Acid Docosahexaenoic Acid Reduces Amyloid Burden in an Aged Alzheimer Mouse Model," *J. Neuroscience* (2005), 25(12), 3032-3040.

Lovaza™ labeling information, Reliant Pharmaceuticals (revised Jun. 2007, 2 pages).

Lovaza™ marketing information (2 pages), 2000.

Luley, C. et al. "Bioavailability of Omega-3 Fatty Acids: Ethylester Preparation are Suitable as Triglyceride Preparations," *Nutrition Lances* (1990), 123-125.

Lungershausen, Y. K. et al. "Reduction of blood pressure and plasma triglycerides by omega-3 fatty acids in treated hypertensives," *Journal of Hypertension* (1994), 12(9), 1041-1045.

Marchioli, R. et al "Early Protection Against Sudden Death by n-3 Polyunsaturated Fatty Acids After Myocardial Infarction," *Circulation* (2002), 105, 1897-1903.

McNeill, G. P. "Lipase-Catalyzed Enrichment of Long-Chain Polyunsaturated Fatty Acids," *JAOCS* (1996), 73(11), 1403-1407.

Merck Index, 11th Ed. (Rahway, NJ. Merck and Co., 1989) p. 925.

Moore, S. R. et al. "Production of Triglycerides Enriched in Long-Chain n-3 Polyunsaturated Fatty Acids from Fish Oil," *JAOCS* (1996), 73(11), 1409-1414.

Nicoud et al. *Proceedings of the 9th International Symposium on Preparative and Industrial Chromatography*, Société Française de Chimie Apr. 1992, pp. 205-220.

Nilsson, W. B. "Supercritical fluid carbon dioxide fractionation of fish oil esters," *Adv. Seafood Chiochem., Pap. Am. Chem. Soc. Annu. Meet.* (1992), Meeting Date 1987, 151-168.

Nordøy, A. "Statins and omega-3 fatty acids in the treatment of dyslipidemia and coronary heart disease," *Minerva medica* (2002), 93(5), 357-363.

Omacor prescribing information from the FDA website: www.fda.gov/cder/foi/label/2004/21654lbl.pdf (9 pages), 2004.

Omacor prescribing information (1 pages), 2004.

Omega-3-Acid Ethyl Esters 90, *European Pharmacopoeia* 5.3 (2006) 3571-3573.

Omega-3-Acid Ethyl Esters 60, *European Pharmacopoeia* 5.4 (2005) 3992-3997.

Perry, R.H. et al., *Chemical Engineers Handbook*, 5th Edition, McGraw-Hill, New York, 1973, 13-55 and 13-56.

Pownall, H. J. et al. "Correlation of serum triglyceride and its reduction by ω-3 fatty acids with lipid transfer activity and the neutral lipid compositions of high-density and low-density lipoproteins," *Atherosclerosis* (1999), 143(2), 285-297.

Proceedings From the Oct. 1987 Fish Oil Seminar, "Rendering Profits," (Alaska Fisheries Development Foundation, Inc. 1987) pp. 1-103.

Product specifications for EPAX 1050TG, 2000.
Product specifications for EPAX 4020EE, 2000.
Product specifications for EPAX 4020TG, 2000.
Product specifications for EPAX 4510TG, 2000.
Product specifications for EPAX 5500EE, 2000.
Product specifications for EPAX 6000EE, 2000.
Product specifications for EPAX 6000TG, 2000.
Product specifications for EPAX 6015EE, 2000.
Product specifications for EPAX 6015TG, 2000.

Reis, G. J. et al. "Effects of Two Types of Fish Oil Supplements on Serum Lipids and Plasma Phospholipid Fatty Acids in Coronary Artery Disease," *Am. J. Cardiology* (1990), 66, 1171-1175.

Shibata, T. et al. "Effects of peroxisome proliferator-activated receptor-a and -g agonist, JTT-501, on diabetic complications in Zucker diabetic fatty rats," *British J. of Pharmocol.* (2000), 130, 495-504.

Shimada, Y. et al. "Purification of Docosahexaenoic Acid by Selective Esterification of Fatty Acids from Tuna Oil with Rhizopus delemar Lipase," *JAOCS* (1997), 74(2), 97-101.

Stalenhoef, A. F. H. et al. "The effect of concentrated n-3 fatty acids versus gemfibrozil on plasma lipoproteins, low density lipoprotein heterogeneity and oxidizability in patients with hypertriglyceridemia," *Atherosclerosis* (2000), 153(1), 129-138.

Takagi, "Fractionation of Polyenoic Acids from Marine Lipids with Lipase," *Am. Oil Chem. Soc.* (1989), 66, 488-489.

Tanaka, Y. et al. "Preparative separation of acylglycerol by centrifugal partition chromatography (CPC). II. Concentration of EPA (eicosapentaenoic acid) and DHA (docosahexaenoic acid) from lipase-hydrolyzed fish oil" *Yukagaku* (1992), 41(4), 312-316, Abstract.

Third Party Observation from corresponding European application No. 03764048.9-2108 dated Sep. 26, 2006.

Treybal, R.E., Mass-Transfer Operations, McGraw-Hill, New York, 1955, pp. 344-353.

Van Dam et al., "Efficacy of concentrated n-3 Fatty Acids in hypertriglyceridaemia—A Comparasion with Gemfibrozil:", Clin. Drug Invest., pp. 175-181, 2001.

Vericel, E. et al. "The influence of low intake of *n*-3 fatty acids on platelets in elderly people," *Atherosclerosis* (1999), 147(1), 187-192.

Xu, X. et al. "Purification and deodorization of structured lipids by short path distillation," *Eur. J. Lipid Sci. Technol.* (2002), 104, 745-755.

Young, W. "Processing of oils and fats," *Chemistry and Industry* (1978), 16, 692-703.

Zinger et al. CA 106:118610 (1986).

Zuyi, et al. "Stability of Microbial Lipase in Alcoholysis of Fish Oil During Repeated Enzyme Use," *Biotechnol. Lett.* (1993), 15(4), 393-398.

Zuyi, et al. "Lipase-catalyzed alcoholysis to concentrate the *n*-3 polyunsaturated fatty acid of cod liver oil," *Enzyme Microb. Technol.* (1993), 15, 601-606.

Database WPI Week 200206, Derwent Publications Ltd., DE 100 24 420 A1.

Ackman, R.G. et al., "The "basic" fatty acid composition of Atlantic fish oils: Potential similarities useful for enrichment of polyunsaturated fatty acids by urea complexation," *J. Am. Oil. Chem. Soc.* (1988) vol. 65, pp. 136-138.

Azhgikhin, I.S. et al., "Obtainment of an esters concentrate of the eicosapentaenoic and decosapentaenoic as a possible substitute of arachiden and Itenol," Pansovietic Institute, Moscow, dated Mar. 14, 1978.

Bang, H.O. et al., "Plasma lipid and lipoprotein pattern in Greenlandic West-coast Eskimos," *Lancet* (1971) vol. 1, pp. 1143-1145.

Bronsgeest-Schoute, H.C. et al., "The effect of various intakes of ω3 fatty acids on the blood lipid composition in healthy human subjects," *Am. J. Clin. Nutr.* (1981) vol. 34, pp. 1752-1757.

Connor, W.E., "Effects of omega-3 fatty acids in hypertriglyceridemic states," *Seminars in Thrombosis and Hemostasis* (1988) vol. 14, pp. 271-284.

Eritsland, J. et al., "Effects of highly concentrated omega-3 polyunsaturated fatty acids and acetylsalicylic acid, alone and combined, on bleeding time and serum lipid profile," *J. Oslo City Hosp.* (1989), vol. 39, pp. 97-101.

Eritsland, J. et al., "The effect of Omacor™ in patients with hypertriglyceridaemia having undergone coronary artery bypass grafting," Final Report, Pronova Biocare, 1994.

"Fish oil, rich in omega-3-acids," European Pharmacopoeia 5.0 (2004) pp. 1595-1598.

Harris, W.S. et al., "The comparative reductions of the plasma lipids and lipoproteins by dietary polyunsaturated fats: Salmon oil versus vegetable oils," *Metabolism* (1983), vol. 32, pp. 179-184.

Hirai, A. et al., "Effect of oral administration of highly purified eicosapentaenoic acid and docosahexaenoic acid on platelet function and serum lipids in hyperlipidemic patients," *Adv. Prostag. Thromb. L.* (1989) vol. 19, pp. 627-631.

Holub et al., "Alterations in molecular species of cholesterol esters formed via plasma lecithin—cholesterol acyltransferase in human subjects consuming fish oil," *Atherosclerosis* (1987) vol. 66, pp. 11-18.

Joseph, J., Ed. "Biomedical Test Materials Program: Production Methods and Safety Manual," NOAA Technical Memorandum NMFS-SEFC-234, pp. 1-3, Oct. 1989.

Kantha, S.S., "Dietary effects of fish oils on human health: A review of recent studies," *Yale J. Biol. Med.* (1987) vol. 60, pp. 37-44.

Kobatake, Y. et al., "Dietary effect of ω-3 type polyunsaturated fatty acids on serum and liver lipid levels in rats," *J. Nutr. Sci. Vitaminol.* (1983) vol. 29, pp. 11-21.

Kobatake, Y. et al., "Differential effects of dietary eicosapentaenoic and docosahexaenoic fatty acids on lowering of triglyceride and cholesterol levels in the serum of rats on hypercholesterolemic diet," *J. Nutr. Sci. Vitaminol.* (1984) vol. 30, pp. 357-372.

Larsen, L.N. et al., "Heneicosapentaenoate (21:5n-3): Its incorporation into lipids and its effects on arachidonic acid and eicosanoid synthesis," *Lipids* (1997) vol. 32, pp. 707-714.

Leaf, A. et al., "Cariovascular effects of n-3 fatty acids," *New Eng. J. Med.* (1988) vol. 318, pp. 549-557.

Maxepa® product information (3 pages).

Medline Plus, "Triglycerides," U.S. National Library of Medicine and National Institutes of Health, 2008.

Mehta, J.T. et al., "Dietary supplementation with omega-3 polyunsaturated fatty acids in patients with stable coronary heart disease," *Am. J. Med.* (1988) vol. 84, pp. 45-52.

Morisaki, N. et al., "In vivo effects of cis-5,8,11,14,17-20:5 (n-3) and cis-4,7,10,13,16,19-22:6(n-3) on serum lipoproteins, platelet aggregation, and lipid metabolism in the aorta of rats," *Tohoku J. Exp. Med.* (1983) vol. 141, pp. 397-405.

Mueller, B.A. et al., "Biological mechanisms and cardiovascular effects of omega-3 fatty acids," *Clin. Pharmacy* (1988) vol. 7, pp. 795-807.

Nestel, P.J. et al., "Suppression by diets rich in fish oil of very low density lipoprotein production in man," *J. Clin. Invest.* (1984) vol. 74, pp. 82-89.

Phillipson, B.E. et al., "Reduction of plasma lipids and lipoproteins in hyperlipidemic patients by dietary w-3 fatty acids," *Am. J. Clin. Nutr.* (1981) vol. 34, p. 629.

Ratnayake, W.M.N. et al., "Preparation of omega-3 PUFA concentrates from fish oils via urea complexation," *Fat Sci. Technol.* (1988), vol. 90, pp. 381-386.

Rote Liste, Eicosapen information, 1987.

Sanders, T.A.B., "The importance of eicosapentaenoic and docosahexaenoic acids," Ch. 7, pp. 101-116, in *The Role of Fats in Human Nutrition*, F.B. Padley et al., Eds., Ellis Horwood Ltd., Chichester, England, 1985.

Sanders, T.A.B. et al., "A comparison of the influence on plasma lipids and platelet function of supplements of ω3 and ω6 polyunsaturated fatty acids," *Br. J. Nutr.* (1983) vol. 50, pp. 521-529.

Sanders, T.A.B. et al., "The influence of different types of ω3 polyunsaturated fatty acids on blood lipids and platelet function in healthy volunteers," *Clinical Science* (1983) vol. 64, pp. 91-99.

Saynor, R. et al., "The long-term effect of dietary supplementation with fish lipid concentrate on serum lipids, bleeding time, platelets and angina," *Atherosclerosis* (1984) vol. 50, pp. 3-10.

Simons, L.A. et al., "On the effects of dietary n-3 fatty acids (Maxepa) on plasma lipids and lipoproteins in patients with hyperlipidaemia," *Atherosclerosis* (1985) vol. 54, pp. 75-88.

Simopoulos, A.P., "Omega-3 fatty acids from fish and fish oils: Nutritional and health effects," *Epitheorese Klinikes Farmakologias Kai Farmakokinetikes, Int. Ed.* (1987) vol. 1, pp. 23-31.

Smith, P. et al., "Influence of highly concentrated n-3 fatty acids on serum lipids and hemostatic variables in survivors of myocardial infarction receiving either oral anticoagulants or matching placebo," *Thromb. Res.* (1989) vol. 53, pp. 467-474.

Swanson, D.R., "Fish oil, Raynaud's Syndrome, and undiscovered public knowledge," *Perspect. Biol. Med.* (1986) vol. 30, pp. 7-18.

Turchetto, E. et al., "Protective role of vitamin E on essential fatty acids," *Acta Vitaminol. Enzymol.* (1982) vol. 4, pp. 267-277, Abstract.

Von Lossonczy, T.O. et al., "The effect of a fish diet on serum lipids in healthy human subjects," *Am. J. Clin. Nutr.* (1978) vol. 31, pp. 1340-1346.

Detwiler, S.B., Jr., "Supplement to Bibliography on Molecular or Short Path Distillation" Oil and Soap (1940) pp. 241-243.

UMEP Chemicals Data Fact Sheet, UNEP Chemicals, Regional Reports of the Regionally Based Assessment of Persistent Toxic Substances Program (2002) (1 page).

Yaws Handbook of Antoine Coefficients for Vapour Pressure, $2^{nd}$ Electronic Edition, 2009 (extract, 6 pages).

\* cited by examiner

PROCESS FOR DECREASING THE AMOUNT OF CHOLESTEROL IN A MARINE OIL USING A VOLATILE WORKING FLUID

FIELD OF THE INVENTION

This invention relates to a process for decreasing the amount of cholesterol in a mixture comprising a marine oil, containing the cholesterol. The present invention also relates to a volatile cholesterol decreasing working fluid, a health supplement and a pharmaceutical, prepared according to the process mentioned above.

BACKGROUND OF THE INVENTION

It is known that cholesterol is an important steroid found in the lipids (fats) in the bloodstream and in all body's cells in mammals. Cholesterol is used to form cell membranes, some hormones and other needed tissues. A mammal will get cholesterol in two ways; the body produces some of it, and the rest comes from products that the mammal consumes, such as meats, poultry, fish, eggs, butter, cheese and whole milk. Food from plants like fruits, vegetables and cereals do not include cholesterol.

Cholesterol and other fats can't dissolve in the blood. They have to be transported to and from the cells by special carriers called lipoproteins, named on basis of their density. Low-density lipoprotein, or LDL, transport cholesterol from the liver to peripheral tissues and LDL transported cholesterol is known as the "bad" cholesterol, because too much LDL cholesterol can clog the arteries to the heart and increase the risk of heart attack. High-density lipoprotein, or HDL, transport cholesterol back to the liver where surplus cholesterol is disposed of by the liver as bile acids. HDL transported cholesterol is known as the "good" cholesterol and high levels of HDL may reduce cholesterol deposits in arteries. For an organism to remain healthy, there has to be an intricate balance between the biosynthesis of cholesterol and its utilization, so that arterial deposition is kept at a minimum.

In e.g. marine oils, cholesterol is stored as "free" respectively as "bound" cholesterol. In the bound form, cholesterol is esterified on the OH-group by a fatty acid.

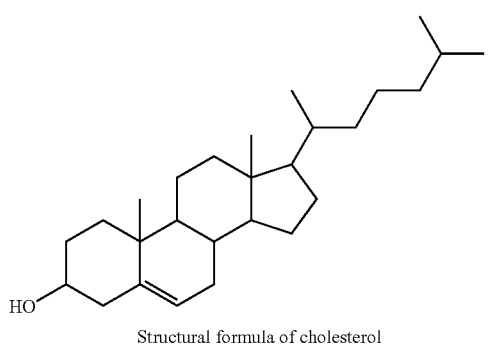

Structural formula of cholesterol

The commercially important polyunsaturated fatty acids in marine oils, such as fish oil, are preferably EPA (eicosapentaenoic acid, C20:5), DHA (docosahexaenoic acid, C22:6). The full nomenclature of these acids according to the IUPAC system is: EPA cis-5,8,11,14,17-eicosapentaenoic acid, DHA cis-4,7,10,13,16,19-docosahexaenoic acid. For many purposes it is necessary that the marine oils should be refined in order to increase the content of EPA and/or DHA to suitable levels, or to reduce the concentrations of, or even eliminate, certain other substances which occur naturally in the raw oil, e.g. cholesterol.

The fatty acids EPA and DHA are also proving increasingly valuable in the pharmaceutical and food supplement industries in particular. It is also very important for fish oils and other temperature sensitive oils (i.e. oils that contains long chain polyunsaturated fatty acids) to keep the load of the temperature as low as possible. Concerning the amount of cholesterol in the oils, it is specially a problem in fish oils and milk fat.

Further, as the link between high serum cholesterol levels and heart disease has become increasingly apparent, cholesterol-free and cholesterol-reduced food products have become more attractive to consumers, and food products that have no or reduced cholesterol are gaining popularity as well as an increasing share of the market. Consequently, removal or reduction of cholesterol in high cholesterol foods has the potential to substantially increase marketability and value.

The removal or reduction of cholesterol in marine oils is not a trivial matter. Several different techniques to accomplish this task have been developed, each with varying levels of success. The content of cholesterol in marine oils will become a much more important parameter for the process industry in the future.

Some methods of treating a fish oil is known from the prior art. Such methods include conventional vacuum steam distillation of fish oils at high temperatures which creates undesirable side reactions, decreases the content of EPA and DHA in the oil and the resulting product has a poor flavour stability and poor resistance to oxidation.

SUMMARY OF THE INVENTION

One object of the invention is to offer an effective process for decreasing the amount of cholesterol in a mixture comprising a marine oil, containing the cholesterol, preferably by decreasing and separating the amount of cholesterol present in free form.

According to a first aspect of the invention, this and other objects are achieved with a process for decreasing the amount of cholesterol in a mixture comprising a marine oil, the marine oil containing the cholesterol, which process comprises the steps of adding a volatile working fluid to the mixture, where the volatile working fluid comprises at least one of a fatty acid ester, a fatty acid amide and a hydrocarbon, and subjecting the mixture with the added volatile working fluid to at least one stripping processing step, in which an amount of cholesterol in the marine oil is separated from the mixture together with the volatile working fluid. Most preferably, the amount of cholesterol present in the marine oil that is separated from the mixture together with the volatile working fluid is constituted by cholesterol in free form. Herein, "an amount" is interpreted to include decreasing of an amount up to almost 100% of cholesterol present in free form, i.e. a substantial removal of cholesterol in free form from a marine fat or oil composition, at low mixture flow rates. The content of bound cholesterol is less affected by the stripping process according to the invention, since cholesterol in bound form has a higher boiling point compared to the working fluid according to the invention.

The use of a volatile working fluid, where the volatile working fluid comprises at least one of a fatty acid ester, a fatty acid amide and a hydrocarbon, or any combination thereof, in a stripping process (or processing step) for decreasing the amount of cholesterol present in a marine oil in free form has a number of advantages.

An advantage of using a volatile working fluid in a stripping process is that the cholesterol present in free form can more easily be stripped off together with the volatile working fluid. Preferably, this is possible as long as the volatile working fluid is essentially equally or less volatile than the cholesterol that shall be removed from the oil mixture. The stripped cholesterol present in free form and the volatile working fluid will be found in the distillate. When the volatile working fluid have the mentioned property, in combination with beneficial stripping process conditions, it is possible to separate, or strip off, almost all cholesterol present in a marine oil in free form more effectively. The effect of adding a volatile working fluid to a marine oil mixture before stripping is larger and also more commercial useful, compared to a general process for decreasing cholesterol in an oil mixture, at higher flow rates. Herein, "high flow rates" is interpreted to include mixture flow rate in the interval of 80-150 kg/h·m$^2$. Under the process conditions mentioned above, the use of a volatile working fluid open up for a much better utilization of the capacity of the process equipment and a more rapid stripping process.

Further, according to the present stripping process it is also possible to decrease an effective amount of cholesterol present in a marine oil in free form at lower temperatures, preferably at a temperature in the interval of 150-220° C., compared to the techniques known from the prior art. It is especially important to keep the temperature as low as possible during processing of marine oils, such as fish oils, and other temperature accommodating oils (i.e. oils comprising long chains of polyunsaturated fatty acids). This is not so critical for oils not included above. In addition, the volatile working fluid according to the invention allows cholesterol present in free form to be stripped off by e.g. molecular distillation even from oils of lower quality, i.e. oil for feed purposes.

In a preferred embodiment of the present invention the volatile working fluid is an organic solvent or solvent mixture with a volatility comparable to the cholesterol in free form. The volatile working fluid of the present invention is at least one of a fatty acid ester, a fatty acid amide, and a hydrocarbon, also including any combinations thereof.

In another preferred embodiment the volatile working fluid comprises at least one fatty acid ester composed of C10-C22 fatty acids and C1-C4 alcohols, or a combination of two or more fatty acid ester each composed of C10-C22 fatty acids and C1-C4 alcohols. Preferably, the volatile working fluid is at least one of amides composed of C10-C22 fatty acids and C1-C4 amines, C10-C22 free fatty acids, and hydrocarbons with a total number of carbon atoms from 10 to 40. Most preferably, the volatile working fluid is a mixture of fatty acids from marine oils, e.g. fish body oil and/or fish liver oil, and/or ethyl or methyl esters of such marine fatty acids.

In another embodiment of the invention a volatile working fluid may be produced by subjecting fats or oils from an available source, for instance fats or oils obtained from at least one of animal, microbial or vegetable origin, to an interesterification process, in which process the triglycerides in the fats or oils are converted into esters of aliphatic alcohols. Additionally, a bio-diesel and/or a mineral oil can be used as a volatile working fluid. In the case when the volatile working fluid is a biodiesel, it can be produced by a process, which is in common use for production of engine fuels (biodiesel), and therefore also known by a man skilled in the art, which process comprises mixing the fat or oil with a suitable amount of aliphatic alcohol, adding a suitable catalyst and heating the mixture for a period of time. Similar esters of aliphatic alcohols may also be produced by a high-temperature catalytic direct esterification process reacting a free fatty acid mixture with the appropriate aliphatic alcohol. The fatty acid ester mixture produced in this manner may be used as a volatile working fluid as it is, but normally the conversion to esters of aliphatic alcohols is not complete, the conversion process preferably leaving some un-reacted non-volatile glycerides in the mixture. Further, some fats or oils may also contain certain amounts of non-volatile, non-glyceride components (e.g. polymers). Such non-volatile components will be transferred to, and mixed with the final product, which product is low in cholesterol, when the fatty acid ester mixture is used as working fluid. A working fluid produced in this manner should therefore be subjected to a distillation, preferably a molecular and/or short path distillation, in at least one step, which distillation process generates a distillate more suitable to be used as a new volatile working fluid.

In addition, the volatile working fluid according to the invention allows cholesterol to be stripped off by e.g. molecular distillation even from oils of lower quality.

In another preferred embodiment of the process, at least one of a fatty acid ester and a fatty acid amide constituting said volatile working fluid is obtained from at least one of a vegetable, microbial and animal fat or oil, being edible or for use in cosmetics. Preferably, the animal fat or oil is a marine oil, e.g. a fish oil or an oil from other marine organism e.g. sea mammals. It is also possible that the fatty acid esters mentioned above can e.g. be a byproduct from distillation of an ethyl ester mixture prepared by ethylation of preferably a fish oil. In the process industry trade with intermediates is increasing and opens up for an extra financial income.

In fish oils cholesterol is typically present in concentrations of 5-10 mg/g, but higher concentrations have been observed. In this case 2-4 mg/g is typically bound cholesterol and 3-6 mg/g is free cholesterol. Free cholesterol can be effectively removed by adding a volatile working fluid prior to at least one of the stripping processes according to the invention.

In another embodiment of the process according to the invention, the marine oil containing saturated and unsaturated fatty acids in the form of triglycerides, and the marine oil is obtained from fish and/or sea mammals. Marine oils that contains no or reduced amounts of cholesterol present in free form are gaining popularity as well as an increasing share of the market.

It is important to note that the invention is not limited to procedures were the working fluid is prepared from the same origin as the oil that is being purified.

In a preferred embodiment of the invention, the ratio of (volatile working fluid):(marine oil) is about 1:100 to 15:100. In a more preferred embodiment the ratio of (volatile working fluid):(marine oil) is about 3:100 to 8:100.

In a preferred embodiment of the invention, said stripping process step is carried out at temperatures in the interval of 120-270° C.

In a most preferred embodiment, the stripping processing step is carried out at temperatures in the interval of 150-220° C. By adding a volatile working fluid to the marine oil mixture at this temperatures the invention surprisingly shows that even termolabile polyunsaturated oils can be treated with good effect, without causing degradation of the quality of the oil.

In another preferred embodiment, the stripping processing step is carried out at a pressure below 1 mbar.

In further preferred embodiment, the stripping processing step is at least one of a thin-film evaporation process, a molecular distillation or a short-path distillation, or any combination thereof. If at least one stripping process step is a thin-film evaporation the process is also carried out at mixture flow rates in the intervall of 30-150 kg/h·m², most preferably in the range of 80-150 kg/h·m². The effect of adding a volatile working fluid to a marine oil mixture before stripping is larger and also more commercial useful, compared to a general process for decreasing cholesterol present in a marine fat or oil in free form at higher flow rates.

By using a stripping process, e.g. a distillation method, for decreasing the amount of cholesterol present in a marine oil in free form, the marine oil mixture comprising a volatile working fluid, it is possible to carry out the stripping processes at lower temperatures, which spare the oil and is at the same time favourable to the end oil product.

Another embodiment of the present invention is a stripping process wherein a working fluid is added to a mixture comprising a marine oil, containing cholesterol, prior to a thin-film evaporation process, and the volatile working fluid comprises at least one of a fatty acid ethyl ester and a fatty acid methyl ester (or any combinations thereof), and subjecting the mixture with the added working fluid to a thin-film evaporation step, in wich an amount of cholesterol present in free form in the marine oil is separated from the mixture together with the volatile working fluid.

In a preferred embodiment according to the invention the stripping process is carried out by a molecular distillation in the following intervals; mixture flow rates in the interval of 30-150 kg/h·m², temperatures in the interval of 120-270° C. and a pressure below 1 .mbar.

In a most preferred embodiment of the invention the molecular distillation is carried out at temperatures in the interval of 150-220° C. and at a pressure below 0.05 mbar, or by a thin-film process, which process is carried out at 80-150 kg/h·m² or at flow rates in the range of 800-1600 kg/h at a heated thin film area of 11 m²; 73-146 kg/h·m². Please note, that the present invention can also be carried out in one or more subsequent stripping processing steps.

In another preferred embodiment of the present invention, a volatile cholesterol decreasing working fluid, for use in decreasing an amount of cholesterol present in a marine oil in free form, the volatile working fluid is comprising at least one of a fatty acid ester, a fatty acid amide and a hydrocarbon, with essentially equally or less volatility compared to the cholesterol that is to be separated from the marine oil, or any combination thereof.

Preferably, the volatile cholesterol decreasing working fluid is generated as a fractionation product. Additionally, the volatile cholesterol decreasing working fluid is a by-product, such as a distillation fraction, from a regular process for production of ethyl and/or methyl ester concentrates. This by-product according to the invention can be used in a new process preferably for fat or oil being edible or for use in cosmetics. More preferably, the volatile cholesterol decreasing working fluid, for use in decreasing an amount of cholesterol present in a marine fat or oil, can be a by-product (a distillate fraction) from a regular process for production of ethyl ester concentrates, wherein a mixture comprising an edible or a non-edible fat or oil, preferably a fish oil, is subjected to an ethylating process and preferably a two-step molecular distillation. In the two-step molecular distillation process a mixture consisting of many fatty acids on ethyl ester form is separated from each other in; a volatile (light fraction), a heavy (residuum fraction) and a product fraction. The volatile fraction from the first distillation is distilled once more and the volatile fraction from the second distillation process is then at least composed of the volatile working fluid, preferably a fatty acid ethyl ester fraction. This fraction consists of at least one of C14 and C16 fatty acids and at least one of the C18 fatty acids from the fat or oil, and is therefore also compatible with the edible or non-edible oil. The fraction can be redistilled one or more times if that is deemed to be suitable. This prepared working fluid can then be used as a working fluid in a new process for decreasing the amount of cholesterol present in a marine oil in free form, wherein the edible or non-edible fats or oils and the marine oil are of the same or different types.

In another preferred embodiment of the invention the volatile working fluid comprises at least one of an ester and/or an amide composed of shorter fatty acids and longer alcohols or amines, or any combination thereof.

In a preferred embodiment of the invention, the volatile cholesterol decreasing working fluid, for use in decreasing an amount of cholesterol present in a marine oil, is preferably a fatty acid ester (e.g. fatty acid ethyl ester or fatty acid methyl ester) or a fatty acid amide obtained from at least one of vegetable, microbial and animal fat or oil, or any combination thereof. Preferably, said animal fat or oil is a marine oil, for instance a fish oil and/or an oil from sea mammals.

In another embodiment of the invention, a volatile cholesterol decreasing working fluid according to the present invention, is used in a process for decreasing the amount of cholesterol in a mixture comprising a marine oil, the marine oil containing the cholesterol, in which process the volatile working fluid is added to the mixture and then the mixture is subjected to at least one stripping processing step, preferably a thin-film evaporation process, a molecular distillation or a short-path distillation or any combination thereof, and in which process an amount of cholesterol present in the marine oil in free form is separated from the oil mixture In a more preferred embodiment, the volatile cholesterol decreasing working fluid is a by-product, such as a distillate fraction, from a regular process for production of ethyl and/or methyl ester concentrates.

In another preferred embodiment a health supplement, or a pharmaceutical containing oil (end) products with a decreased amount of cholesterol, preferably strongly limited amounts of cholesterol present in free form, prepared according to at least one of the previously mentioned processes is disclosed. For the pharmaceutical and food supplement industries, marine oils often is processed in order to increase the content of EPA and/or DHA to suitable levels and the removal or reduction of cholesterol have the potential to substantially increase marketability and value. Therefore, the present invention also discloses a health supplement and a pharmaceutical respectively, containing at least a marine oil, such as fish oil, which marine oil is prepared according to the previously mentioned process, in order to decrease the total amount of cholesterol present in the marine oil. It shall be noted that the invented process may also be used for marine oils which has not been processed in order to increase the content of EPA and/or DHA to suitable levels.

In another embodiment of the invention the pharmaceutical and/or health supplement is preferably intended for treating cardiovascular diseases (CVD) and inflammatory diseases, but they also have positive effects on other CVD risk factors such as the plasma lipid profile, hypertension and vascular inflammation. In more preferred embodiment of the invention the pharmaceutical and/or health supplement comprises at least one of EPA/DHA triglycerides/ethyl esters and is intended for a range of potential therapeutic applications including; treatment of hypertriglyceridaemia, secondary prevention of myocardial infarction, prevention of atherosclerosis, treatment of hypertension, mental disorders and/or kidney disease and to improve children's learning ability.

Preferably, the pharmaceutical and/or health supplement prepared according to at least one of the previously mentioned processes is based on fish oil.

Further, the present invention also disclose a marine oil product, prepared according to at least one of the previously mentioned processes. Preferably, the marine oil product is based on fish oil or a fish oil composition.

In another preferred embodiment the stripping process is followed by a trans-esterification process. Preferably, the stripping processing step is followed by the steps of; subjecting the stripped marine oil mixture to at least one trans-esterification reaction with a $C_1$-$C_6$ alcohol under substantially anhydrous conditions, and in the presence of a suitable catalyst (a chemical catalyst or an enzyme) to convert the fatty acids present as triglycerides in the marine oil mixture into esters of the corresponding alcohol, and thereafter subjecting the product obtained in the step above to at least one or more distillations, preferably one or more molecular distillations.

After the trans-esterification reaction some glycerides and most of the bound cholesterol will remain unreacted. Both the unreacted glycerides and the bound (esterified) cholesterol will have higher boiling points than the valuable esters of polyunsaturated fatty acids, and will therefore be concentrated in the residue (waste) fraction. Thereby a substantial reduction in bound cholesterol can be obtained in the distillate (product) fraction.

By combining the steps of first stripping the cholesterol in free form from the marine oil triglycerides using a volatile working fluid, followed by catalysed esterification of the marine oil with a $C_1$-$C_6$ alcohol under substantially anhydrous conditions, and thereafter distillation under conditions suitable to enrich the bound cholesterol in the residium (waste) fraction, a fatty acid ester product with a significant reduction in both free and bound cholesterol can be produced. More preferably, said $C_1$-$C_6$ alcohol is ethanol.

In another preferred embodiment of the invention the volatile working fluid comprises at least one of an ester, amides and/or esters composed of longer fatty acids and shorter alcohols or amines, or any combination thereof.

BRIEF DESCRIPTION OF THE DRAWINGS

The advantages and details of the present invention will become apparent from the following description when taken in conjugation with the accompanying drawings, in which.

DETAILED DESCRIPTION OF PREFERRED EMBODIMENTS

Figure 1:
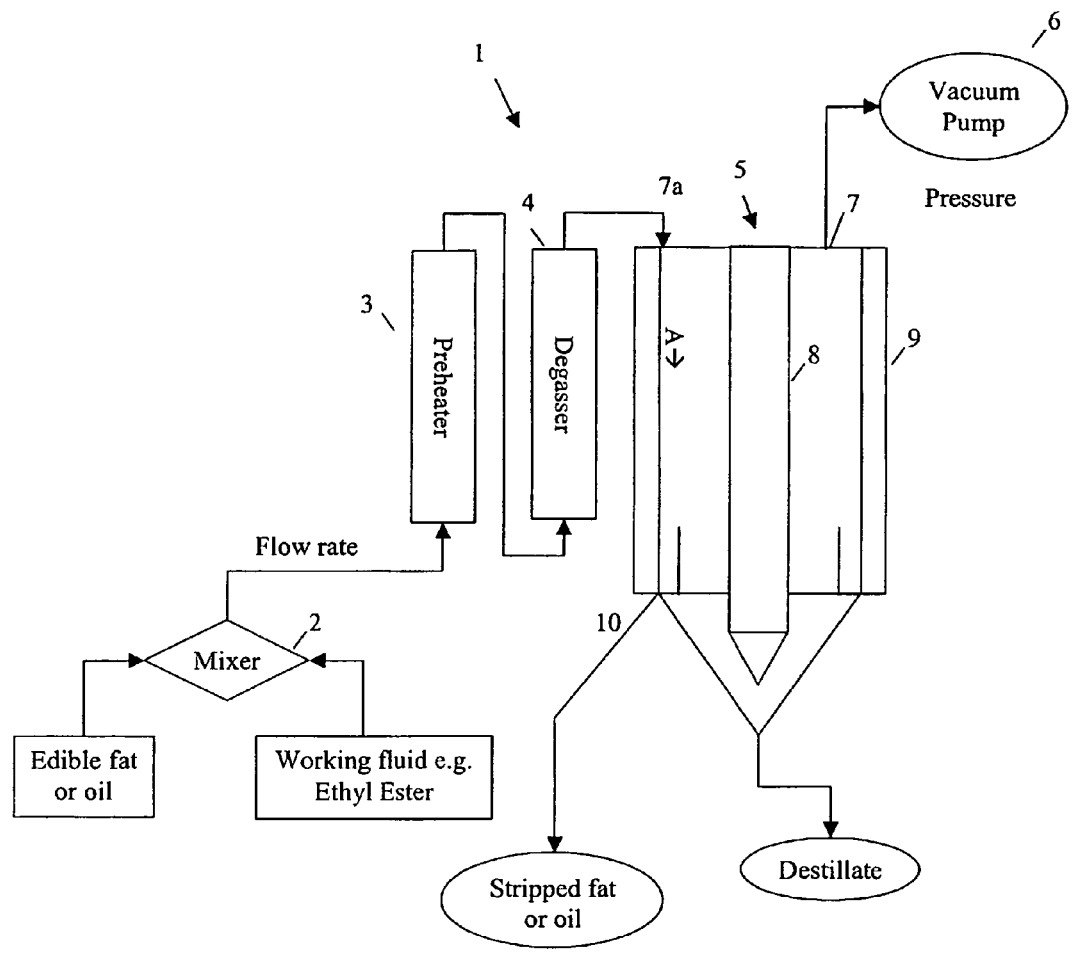
FIG. 1 is a schematic flow chart of one embodiment illustrating a method for decreasing the amount of cholesterol in a marine oil, by adding a volatile working fluid prior to a molecular distillation.

A number of preferred embodiments of the process for decreasing the amount of cholesterol in a mixture comprising a volatile working fluid and a marine oil, containing the cholesterol, will be disclosed below.

A first embodiment of a process for decreasing the amount of cholesterol in a marine oil by adding a volatile working fluid prior to a molecular distillation is presented in FIG. 1. The starting marine oil in the first embodiment of the invention is a fish oil whether freshly refined, reverted or mixtures thereof characterized by an initial or native cholesterol level. The exact amount of cholesterol varies depending upon such factors as fish species, seasonality, geographical catch location and the like.

As used herein the term molecular distillation is a distillation process performed at high vacuum and preferably low temperature (above 120° C.). Herein, the condensation and evaporation surfaces are within a short distance from each other, so as to cause the least damage to the oil composition.

The molecular distillation plant (1) illustrated in FIG. 1, comprises a mixer (2), a pre-heater (3), a degasser (4), a distillation unit (5) and a vacuum pump (6). In accordance with this embodiment, a volatile working fluid comprising an ethyl ester fraction (6% relative to the oil) is added to a fish oil mixture and blended in a mixer (2). The fish oil mixture is then optionally passed through a means for controlling the oil feed rate, such as an ordinary throttling valve. The fish oil mixture is then preheated with a heating means (3) such as a plate heat exchanger to provide a preheated fish oil mixture. The mixture is then passed through a degassing step (4) and admitted into the short path evaporator (5), a tube (7) including the condensation (8) and evaporation (9) surface. The fish oil mixture to be concentrated is picked up as it enters the tube (7a) by rotating blades (not shown). The blades extend nearly to the bottom of the tube and mounted so that there is a clearance of about 1.3 mm between their tips and the inner surface of the tube. In addition, the blades are driven by an external motor. The fish oil mixture is thrown against the tube wall and is immediately spread into a thin film and is forced quickly down (A) the evaporation surface. The film flows down by gravity, and as it falls the light and heavy fractions are separated because of differences in boiling point.

Heated walls and high vacuum strips off the volatile working fluid together with the cholesterol, i.e. the more volatile components (distillate) is derived to the closely positioned internal condenser (8), the less volatile components (residue) continues down the cylinder. The resulting fraction, the stripped fish oil mixture containing at least the fatty acids EPA and DHA is separated and exit through an individual discharge outlet (10).

In a second embodiment a falling film evaporator is used. In falling film evaporators liquid and vapours flow downwards in parallel flow. The liquid to be concentrated, herein the fish oil mixture, is preheated to boiling temperature. The oil mixture enters the heating tubes via a distribution device in the head of the evaporator, flows downward at boiling temperature, and is partially evaporated. This gravity-induced downward movement is increasingly augmented by the co-current vapour flow. Falling film evaporators can be operated with low temperature differences between the heating media and the boiling liquid, and they also have short product contact times, typically just a few seconds per pass.

In a third embodiment of the invention the process is carried out by a short path distillation, which includes the use of a short path evaporator that integrates the features and advantages of thin film or wiped film evaporators but adds internal condensing for applications. Short path evaporators are widely used in fine and specialty chemicals for thermal separation of intermediates, concentration of high value products, and molecular distillation under fine vacuum conditions. Their key features make them uniquely suitable for gentle evaporation and concentration of heat sensitive products at low pressures and temperatures.

In a fourth embodiment of the invention the stripping process is followed by the steps of subjecting the stripped marine oil mixture to at least one trans-esterification reaction with a $C_1$-$C_6$ alcohol under substantially anhydrous conditions and thereafter subjecting the product obtained in the step above to at least one or more distillations, preferably one or more molecular distillations. The key step in all trans-esterification reactions is the reaction between an ester mixture, composed of fatty acids bound to an alcohol A, and an alcohol B where the reaction products are an ester mixture, composed of the same fatty acids bound to alcohol B, and alcohol A as shown in this general formula:

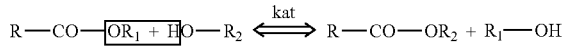

The reaction is preferably catalysed and the reaction is an equilibrium and the yield of the expected fatty acid ester is to a large extent controlled by the concentration of the alcohols. Herein, for instance the stripping process is followed by a catalysed trans-esterification of marine oil triglycerides. The separation of the ethyl ester fraction from the fraction containing the unreacted glycerides and bound cholesterol is suitably carried out by at least one of a molecular distillation technique, whereby the less volatile residual mixture can be readily removed from the relatively volatile ethyl esters.

It should be understood that many modifications of the above embodiments of the invention are possible within the scope of the invention such as the latter is defined in the appended claims. It will be apparent for one skilled in the art that various changes and modifications, i.e. other combinations of temperatures, pressures, and flow rates during the stripping process can be made therein without departing from the spirit and scope thereof.

EXAMPLES

The invention will now be illustrated by means of the following non-limiting example. This example is set forth merely for illustrative purposes and many other variations of the process may be used. The example below summarize some results from different purification of fish oils by molecular distillation.

Example 1

A Stripping Process for Decreasing the Amount of Cholesterol Present in a Fish Oil Mixture in Free Form with Respectively without Using a Volatile Working Fluid This example shows an industrial scale process for decreasing the amount of cholesterol in a refined fish oil mixture in free form, with and without adding a volatile working fluid to the fish oil mixture, and subjecting the mixture to a molecular distillation process.

Herein, an Anchovy oil from Peru, with a fatty acid composition of 18% EPA and 12% DHA was used. The oil contains about 9 mg cholesterol/g fish oil, of which 6 mg/g was constituted by cholesterol present in free form and about 3 mg/g in bound form. In tests 1 and 3 a volatile working fluid constituted by a fatty acid ethyl ester mixture, 6% ethyl ester relative to the fish oil, i.e. the ratio of (volatile working fluid):(fish oil) about 6:100, was added to the fish oil mixture before subjecting the mixture to a molecular distillation process. All tests below were carried out at mixture flow rates of 900 or 400 kg/h in a molecular distillation unit with an evaporation surface of 11 m². Test 1 and 2 were carried out at a temperature of 210° C. and at a mixture flow rate of 900 kg/h. Test 3 and 4 were carried out at a lower temperature, 205° C., and at a lower flow rate, 400 kg/h. The amount of cholesterol present in the fish oil mixture in free form was analysed by a method based on standard high performance liquid chromatographic analyses.

TABLE 1

Amounts of cholesterol present in a fish oil in free form after molecular distillation

| Test | Temp. (° C.) | Flow rate (kg/h) | % added ethyl ester | Free cholesterol (mg/g) |
|---|---|---|---|---|
| 1 | 210 | 900 | 6 | 1.4 |
| 2 | 210 | 900 | 0 | 2.4 |
| 3 | 205 | 400 | 6 | 0.2 |
| 4 | 205 | 400 | 0 | 0.4 |

The results in the table above illustrates that it is possible to decrease (to separate) an amount of free cholesterol in a marine oil more effective by adding a volatile working fluid to a marine oil composition and thereafter subjecting the fish oil composition to a stripping processing step according to the invention. It is important to note that the effect by adding a volatile working fluid to a marine oil composition, before subjecting at least one stripping processing step, is better, and more interesting, when the stripping process is carried out at higher mixture flow rates, preferably flow rate in the interval of 80-150 kg/h·m². Under these conditions, the use of a volatile working fluid opens up for a much better utilization of the capacity of the process equipment and a more rapid stripping process.

Another advantage by using a volatile working fluid according to the invention is that the stripping effect is satisfactory at low temperatures [temperatures in the interval of 120-220° C.] for marine oils. Namely, for marine oils, such as fish oils, and other temperature accommodating oils (oils comprising long chains of polyunsaturated fatty acids) it is important to keep the temperature load during the processes as low as possible. But, this is less important for other oils not mentioned above.

Further, the effect of adding a volatile working fluid, compared with no adding of the same, is less noticeable in the case when the stripping process is carried out at low mixture flow rates [i.e. flow rates<30 kg/h·m²]. But on the other hand, it is not known commercially interesting to carry out a stripping process using low feed rates and relatively high temperatures because the stripping process will take too long to finish. Additionally, today it is a problem for the marine oil industry to find effective and rapid techniques that are able to decrease the amount of cholesterol in marine oils at higher flow rates.

The tests above also show that the amount of free cholesterol is reduced from about 6 mg/g to about 1.4 mg/g by adding a volatile working fluid to a fish oil mixture prior to a molecular distillation process, which process being carried out at a temperature of 210° C. and at a mixture flow rate of 900 kg/h pr. Here, the amount of cholesterol in free form is decreased with about 75-80%.

When the stripping process is carried out at 900 kg/h the amount of free cholesterol is reduced further compared to the stripping process where no ethyl ester (working fluid) has been added, at the same flow rate. Note that the content of bound cholesterol is less affected by the stripping process according to the invention. Additionally, the use of very high temperatures, i.e. temperatures above 270° C., isn't of interest. Such temperatures will cause damage to the oil. Too high temperatures also can be harmful for the production equipment.

Further, the amount (%) of addition of ethyl ester is also of importance. Addition of at least 4% ethyl ester or an ethyl ester fraction has also generated good results. Preferably, the ratio of (volatile working fluid):(marine oil) is about 1:100 to 15:100 and more preferably, the ratio of (volatile working fluid):(marine oil) is about 3:100 to 8:100.

While the invention has been described in detail and with reference to specific embodiments thereof, it will be apparent for one skilled in the art that various change and modifications can be made therein without departing from the spirit and scope thereof.

DEFINITIONS

As used herein the term marine oil also includes marine fat and a fermented or refined product containing at least n−3 polyunsaturated fatty acids, predominately EPA and DHA from a raw marine oil. Further, the marine oil is preferably oil from at least one of fish, shellfish (crustaceans) and sea mammals, or any combination thereof. Non limiting examples of fish oils are Menhaden oil, Cod Liver oil, Herring oil, Capelin oil, Sardine oil, Anchovy oil and Salmon oil. The fish oils mentioned above may be recovered from fish organs, e.g. cod liver oil, as well as from the meat of the fish, from the whole fish or from fish waste. Additionally, the term "oil and fat" means fatty acids in at least one of the triglyceride and phospholipid forms. Generally, if the start material in the stripping process is a marine oil, the oil may be any of raw or partially treated oil from fish or other marine sources and which contains fatty acids, including polyunsaturated fatty acids, in the form of triglycerides. Typically, each triglyceride molecule in such a marine oil will contain, more or less randomly, different fatty acid ester moieties, be the saturated, monounsaturated or polyunsaturated, or long chain or medium chain. Further, examples of vegetable oils or fats are corn oil, palm oil, rapeseed oil, soybean oil, sunflower oil and olive oil. Additionally, the marine fat or oil may be pre-processed in one or several steps before constituting the start material in the stripping process as described above.

As used herein the term edible means edible for humans and/or animals. Additionally, as used herein the term "for use in cosmetics" means an oil or a fat that can be used in products that contributes to enhance humans appearance and/or health, e.g. cosmetic and/or beauty care products. Further, a fat or an oil, being edible or for use in cosmetics, according to the invention can also be a blend of e.g. microbial oils, fish oils, vegetable oils, or any combination thereof.

As used herein the term microbial oils also includes "single cell oils" and blends, or mixtures, containing unmodified microbial oils. Microbial oils and single cell oils are those oils naturally produced by microorganisms during their lifespan.

As used herein the term working fluid is interpreted to include a solvent, a solvent mixture, a composition and a fraction, e.g. a fraction from a distillation process, that has a suitable volatility, comprising at least one of esters composed of C10-C22 fatty acids and C1-C4 alcohols, amides composed of C10-C22 fatty acids and C1-C4 amines, C10-C22 free fatty acids, mineral oil, hydrocarbons and bio-diesel.

As used herein the term essentially equally or less volatile is interpreted to include that the volatile working fluids having a suitable volatility in relation to the volatility of the cholesterol present in the marine oil in free form that is to be stripped off from the marine mixture. Further, commonly this is the case when the volatility of the working fluid is the same or lower than the volatility of the cholesterol present in free form. However, the term essentially equally or less volatile is also intended to include the case when the volatile working fluid is somewhat more volatile than the cholesterol in free form.

Further, as used herein the term stripping is interpreted to include a general method for removing, separating, forcing or flashing off gaseous compounds from a liquid stream. In addition, the term "stripping processing step" preferable herein is related to a method/process for decreasing the amount of cholesterol in a marine oil or fat by one or more distilling or distillation processes, e.g. short path distillations, thin-film distillations (thin-film stripping or thin-film (steam) stripping), falling-film distillations and molecular distillations, and evaporation processes.

As used herein the term "together with", means that the volatile working fluid will be stripped off together with, combined with, or adhering the cholesterol, namely that the cholesterol will accompany the working fluid.

As used herein the term health supplement is interpreted to include food and food supplement to animals and/or humans, fortification of food, dietary supplement, functional (and medical) food and nutrient supplement.

As used herein the term "treating" means both treatment having a curing or alleviating purpose and treatment having a preventive purpose. The treatment can be made either acutely or chronically. In addition, as used herein the term pharmaceutical means pharmaceutical preparations and compositions, functional food (foodstuff having an increased value) and medical food. A pharmaceutical preparation according to the present invention may also comprise other substances such as an inert vehicle or a pharmaceutically acceptable adjuvance, carriers, preservatives etc., which all are well-known to those skilled in the art.

As used herein the term "oils with a low quality" preferably means that the oil contains high amounts of free fatty acids, that makes them less useful for nutritional purposes and that traditional alkaline refining in such oils is complicated and costly. Additionally, as used herein, the term mineral oil is interpreted to include mineral oil products such as e.g. fractions from distillation processes and white spirit. As used herein hydrocarbons is interpreted to include organic compounds, that are relatively large molecules composed mainly of carbon and hydrogen. They can also include nuclei of nitrogen, phosphorus, sulphur, and chlorine, among others.

Further, the method according to the invention is also applicable to a variety of sterols including cholesterol. Most of these sterols can, when present on free form, be separated from a marine oil by the described technique as long as the volatile working fluid is essentially equally or less volatile than the sterol in free form that is to be separated from the marine oil mixture.

The invention claimed is:

1. A process for decreasing the concentration of cholesterol in a marine oil in a pharmaceutical composition, the marine oil comprising cholesterol in free form, said process comprising:
   a) adding a volatile working fluid to the marine oil, wherein the volatile working fluid comprises at least one fluid chosen from fatty acid esters, fatty acid amides, and hydrocarbons, and
   b) subjecting the mixture of marine oil and volatile working fluid from step (a) to at least one stripping processing step, wherein an amount of the cholesterol present in the marine oil in free form is separated from the mixture together with the volatile working fluid; and
wherein said pharmaceutical composition is not a health supplement.

2. The process according to claim 1, wherein the volatile working fluid is essentially equally or less volatile than the cholesterol in free form that is to be separated from the marine oil mixture.

3. The process according to claim 1, wherein the fatty acid moieties of said fatty acid esters and fatty acid amides are obtained from a fat or oil obtained from at least one of vegetable, microbial, and animal origins.

4. The process according to claim 3, wherein the animal fat or oil is a marine oil.

5. The process according to claim 1, wherein the volatile working fluid comprises at least one fatty acid ester composed of a C10-C22 fatty acid esterified with a C1-C4 alcohol.

6. The process according to claim 1, wherein the marine oil comprises at least one fatty acid chosen from saturated fatty acids in the form of triglycerides and unsaturated fatty acids in the form of triglycerides, and wherein the marine oil is obtained from fish or sea mammals.

7. The process according to claim 1, wherein the ratio of (volatile working fluid) (marine oil) ranges from about 1:100 to 15:100.

8. The process according to claim 7, wherein the ratio of (volatile working fluid):(marine oil) ranges from about 3:100 to 8:100.

9. The process according to claim 1, wherein said at least one stripping processing step is carried out at a temperature in the range of 120-270° C.

10. The process according to claim 1, wherein said at least one stripping processing step is carried out at a temperature in the range of 150-220° C.

11. The process according to claim 1, wherein said at least one stripping processing step is carried out at a pressure below 14 mbar.

12. The process according to claim 1, wherein said at least one stripping processing step is chosen from thin-film evaporation processes, molecular distillations, short-path distillations, and any combinations thereof.

13. The process according to claim 12, wherein the thin-film evaporation process is carried out at a mixture flow rate in the range of 30-150 kg/h·m².

14. The process according to claim 1, wherein said at least one stripping processing step is carried out at a mixture flow rate in the range of 80-150 kg/h·m².

15. The process according to claim 1, wherein the volatile working fluid is a distillate fraction from a process in which a mixture comprising at least one of ethyl and methyl esters of fatty acids obtained from marine oil is fractionated by distillation.

16. The process according to claim 1 wherein the marine oil further comprises cholesterol in bound form, and wherein the at least one stripping processing step is followed by the steps:

c) subjecting the stripped marine oil to at least one transesterification reaction with a $C_1$-$C_6$ alcohol under substantially anhydrous conditions; and d) subjecting the transesterified marine oil from step (c) to at least one distillation procedure that yields a distillate marine oil fraction and a residue marine oil fraction, wherein the distillate marine oil fraction has concentrations of free and bound cholesterol lower than in the residue fraction.

17. The process according to claim 16, wherein said $C_1$-$C_6$ alcohol is ethanol.

18. A process for decreasing the concentration of cholesterol in a marine oil comprising cholesterol in free form comprising:

a) adding a volatile working fluid to the marine oil, wherein the volatile working fluid comprises at least one fluid chosen from fatty acid esters, fatty acid amides, and hydrocarbons, and b) subjecting the mixture of marine oil and volatile working fluid from step (a) to at least one stripping processing step, wherein an amount of the cholesterol present in the marine oil in free form is separated from the mixture together with the volatile working fluid;

wherein said process decreases the concentration of cholesterol in free form in the pharmaceutical composition to 1.4 mg/g to 3 mg/g.

19. The process according to claim 18, wherein the volatile working fluid is essentially equally or less volatile than the cholesterol in free form that is to be separated from the marine oil mixture.

20. The process according to claim 18, wherein the fatty acid moieties of said fatty acid esters and fatty acid amides are obtained from a fat or oil obtained from at least one of vegetable, microbial, and animal origins.

21. The process according to claim 20, wherein the animal fat or oil is a marine oil.

22. The process according to claim 18, wherein the volatile working fluid comprises at least one fatty acid ester composed of a C10-C22 fatty acid esterified with a C1-C4 alcohol.

23. The process according to claim 18, wherein the marine oil comprises at least one fatty acid chosen from saturated fatty acids in the form of triglycerides and unsaturated fatty acids in the form of triglycerides, and wherein the marine oil is obtained from fish or sea mammals.

* * * * *

UNITED STATES PATENT AND TRADEMARK OFFICE
CERTIFICATE OF CORRECTION

PATENT NO. : 7,678,930 B2  Page 1 of 1
APPLICATION NO. : 10/520897
DATED : March 16, 2010
INVENTOR(S) : Sverre Sondbø et al.

It is certified that error appears in the above-identified patent and that said Letters Patent is hereby corrected as shown below:

Claim 11, col. 13, line 27, "14 mbar" should read --1 mbar--.

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,678,930 B2 | Page 1 of 1 |
| APPLICATION NO. | : 10/520897 | |
| DATED | : March 16, 2010 | |
| INVENTOR(S) | : Sondbo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 855 days.

Signed and Sealed this

Thirtieth Day of November, 2010

David J. Kappos
*Director of the United States Patent and Trademark Office*